United States Patent
Heikkilä et al.

(10) Patent No.: US 7,022,239 B2
(45) Date of Patent: Apr. 4, 2006

(54) METHOD FOR FRACTIONATING LIQUID MIXTURES

(75) Inventors: Heikki Heikkilä, Espoo (FI); Jarmo Kuisma, Lohja AS (FI); Jari Lewandowski, Siuntio (FI); Hannu Paananen, Kantvik (FI); Vili Ravanko, Clinton, IA (US); Jukka Rinne, Kirkkonummi (FI)

(73) Assignee: Danisco Sweeteners Oy, Espoo (FI)

( * ) Notice: Subject to any disclaimer, the term of this patent is extended or adjusted under 35 U.S.C. 154(b) by 136 days.

(21) Appl. No.: 10/389,059

(22) Filed: Mar. 14, 2003

(65) Prior Publication Data

US 2003/0217970 A1 Nov. 27, 2003

Related U.S. Application Data

(63) Continuation of application No. PCT/EP01/10035, filed on Aug. 30, 2001.

(30) Foreign Application Priority Data

Sep. 15, 2000 (GB) .................................. 0022713

(51) Int. Cl.
*B01D 15/08* (2006.01)

(52) U.S. Cl. .................. 210/659; 210/198.2; 127/46.2; 127/46.3

(58) Field of Classification Search ................ 210/659, 210/635, 656, 198.2; 127/46.2, 46.3
See application file for complete search history.

(56) References Cited

U.S. PATENT DOCUMENTS

| 3,686,117 A | * | 8/1972 | Lauer et al. .................. 127/55 |
| 3,960,520 A | | 6/1976 | Allen .............................. 65/59 |
| 4,070,284 A | * | 1/1978 | Fujita et al. ................. 210/659 |
| 4,366,060 A | * | 12/1982 | Leiser et al. ................ 210/635 |

(Continued)

FOREIGN PATENT DOCUMENTS

| EP | 0 663 224 A1 | 7/1995 | ................. 210/659 |
| EP | 1 003 036 A1 | 5/2000 | ................. 210/659 |
| GB | 1236937 | 6/1971 | ................. 210/659 |
| WO | WO 96/10650 | 4/1996 | ................. 210/659 |

(Continued)

*Primary Examiner*—Ernest G. Therkorn
(74) *Attorney, Agent, or Firm*—Scully, Scott, Murphy & Presser, P.C.

(57) ABSTRACT

The present invention relates to a method of fractionating liquid mixtures or solutions, comprising the steps of subjecting a feed in the form of a liquid mixture or solution to a first chromatographic separation, thereby recovering at least a fraction (A) and a fraction (B) both containing a first component or product, subjecting a mixture or solution derived from or comprising said fraction (A) to a second chromatographic separation, thereby recovering at least a fraction (C) rich in said first component or product and subjecting a mixture or solution derived from or comprising said fraction (B) to a third chromatographic separation, thereby recovering at least a fraction (D) also rich in said first component or product, and whereby at least two fractions are recovered from the second and third chromatographic separations.

36 Claims, 1 Drawing Sheet

U.S. PATENT DOCUMENTS

| | | | |
|---|---|---|---|
| 4,454,043 A | * 6/1984 | Ting et al. | 210/659 |
| 4,631,129 A | * 12/1986 | Heikkila | 210/635 |
| 4,724,081 A | * 2/1988 | Kawahara et al. | 210/659 |
| 5,122,275 A | * 6/1992 | Rasche | 210/659 |
| 5,198,120 A | 3/1993 | Masuda et al. | 210/659 |
| 5,281,256 A | * 1/1994 | Sacks et al. | 95/86 |
| 5,637,225 A | 6/1997 | Heikkilä et al. | 210/659 |
| 5,730,877 A | * 3/1998 | Heikkila et al. | 210/659 |
| 6,379,554 B1 | * 4/2002 | Kearney et al. | 210/659 |

FOREIGN PATENT DOCUMENTS

| | | | |
|---|---|---|---|
| WO | WO 97/45185 | 12/1997 | 210/659 |
| WO | WO 98/32514 | * 7/1998 | 210/659 |

* cited by examiner

METHOD FOR FRACTIONATING LIQUID MIXTURES

CROSS-REFERENCE TO RELATED APPLICATIONS

This application is a continuation of International Application No. PCT/EP01/10035, filed on Aug. 30, 2001.

The present invention relates to a method for fractionating liquid mixtures by way of multiple chromatographic separation.

Chromatographic separation has proven to be a very valuable method for separating liquid mixtures which otherwise cannot or not sufficiently be split into their individual components. While some success has been made with chromatographic separations in large scale operations, there still exists a need for more efficient methods and methods which allow for the separation of components that exhibit a rather similar separation behaviour. There also exists a need for methods which allow for the recovery of multiple products and/or products with very high purity.

The above considerations are particularly true for simulated moving bed separation techniques. This type of chromatographic separation has been successfully employed in the large scale separation of such diverse feed stock material as sulphite cooking liquors, molasses, vinasse, glucose-fructose syrup, maltose syrup, maltitol syrup, starch hydrolyzate syrups and lactose-lactulose syrup.

Generally speaking, simulated moving bed processes may be continuous processes or sequential processes. A continuous moving bed process has, for example, been disclosed in U.S. Pat. No. 2,985,589. The method disclosed in this patent makes use of several partial packed beds which are connected so as to form a single loop. The feed mixture to be fractionated is introduced into one partial packed bed and eluent is introduced into another partial packed bed. The feeding points for the feed and the eluent as well as the withdrawal points are cyclically shifted in the downstream direction of the packing material bed. At the same time a continuous circulation is maintained. In this process two product fractions are withdrawn essentially simultaneously from the system. A similar method is also described in U.S. Pat. No. 4,412,866.

Examples for sequential simulated moving bed processes can be found in GB 2 240 053 and U.S. Pat. No. 4,332,623 as well as U.S. Pat. Nos. 4,379,751 and 4,970,002.

With such single loop SMB methods, considerable success has been made in the field of separation and in particular, the separation of molasses, cooking liquors and fructose syrups. There still exists however a need for improved product yield and purity, as well as for a separation technology that allows for the isolation of more than two products from a given feed. Chromatographic separations using one or more loops are also known from U.S. Pat. No. 6,093,326.

As far as the improvement of the product yield and purity is concerned, two step processes have proven successful. A process of this kind is disclosed in the present applicant's U.S. Pat. No. 5,795,398, which concerns the separation of sucrose and a second dissolved component from a sucrose containing solution. According to this process, the feed solution in the first step is subjected to an SMB process to yield a first fraction comprising/containing sucrose and a fraction enriched with a dissolved component. The second fraction enriched with the dissolved component is then subjected to a further chromatographic fractionation, that may be a further SMB type fractionation or a batch type fractionation, to yield a second sucrose enriched fraction and a fraction enriched with said second dissolved component.

A related process is disclosed in WO 98/32514. According to this disclosure a feed containing a first component and a second component is fractionated into a first fraction enriched with said first component and a second fraction enriched with said second component. In a subsequent second chromatographic separation procedure, the fraction enriched with said first component is then fractionated into a fraction further enriched with said first component and a residue fraction.

As far as the fractionation of a feed into more than two products is concerned, Kishihara et al. in Biosci. Biotech. Biochem., 56 (5) 801–802, 1992 and in the International Sugar Journal, 1992, volume 94, No. 1128, 305 have shown that in principle it is possible to use the single loop SMB technique to isolate more than two products. However, with single loop continuous SMB technology it is not generally easy to obtain (to separate) more than two products with high yield.

Another way of producing more than two fractions with SMB technology has been discussed in the Sugar Journal April 1997, page 20, where it was proposed to use coupled loop SMB chromatography for the generation of more than two products from a given feed. This is accomplished by fractionating the feed in a first loop into two fractions enriched with different components and subsequently subjecting each of these fractions to a further chromatographic separation to thereby yield more than two products.

Despite the substantial progress made in separation technology in the recent past, there still exists a need for further improved product yield and purity, as well as for more versatile separation methods capable of separating a multitude of products from a given feed.

In particular, there is a need for the separation of three or more compounds, which elute very close to each other (small difference in retention times) in the dry solids profile with high purity and high yield. Especially, in cases where the compound eluting in the middle strongly overlaps with the other two components, a separation with prior art techniques with high purity and high yields is not possible.

The present invention provides a method for fractionating liquid mixtures which satisfies these needs. The method according to the present invention resides in a process involving a first step, wherein a feed in the form of a liquid mixture or solution is subjected to a first chromatographic separation. From this first chromatographic separation at least a fraction (A) and a fraction (B) are recovered. Both of these fractions contain a first component or product.

In a second step of the method according to the present invention, said fraction (A) and said fraction (B) or mixtures containing the same or mixtures derived therefrom are then separately subjected to further chromatographic separation in a second and a third chromatographic separation. Said second and said third chromatographic separations yield at least a fraction (C) and a fraction (D), both of which are rich in said first component.

DESCRIPTION OF THE PREFERRED EMBODIMENTS

Figure 1:
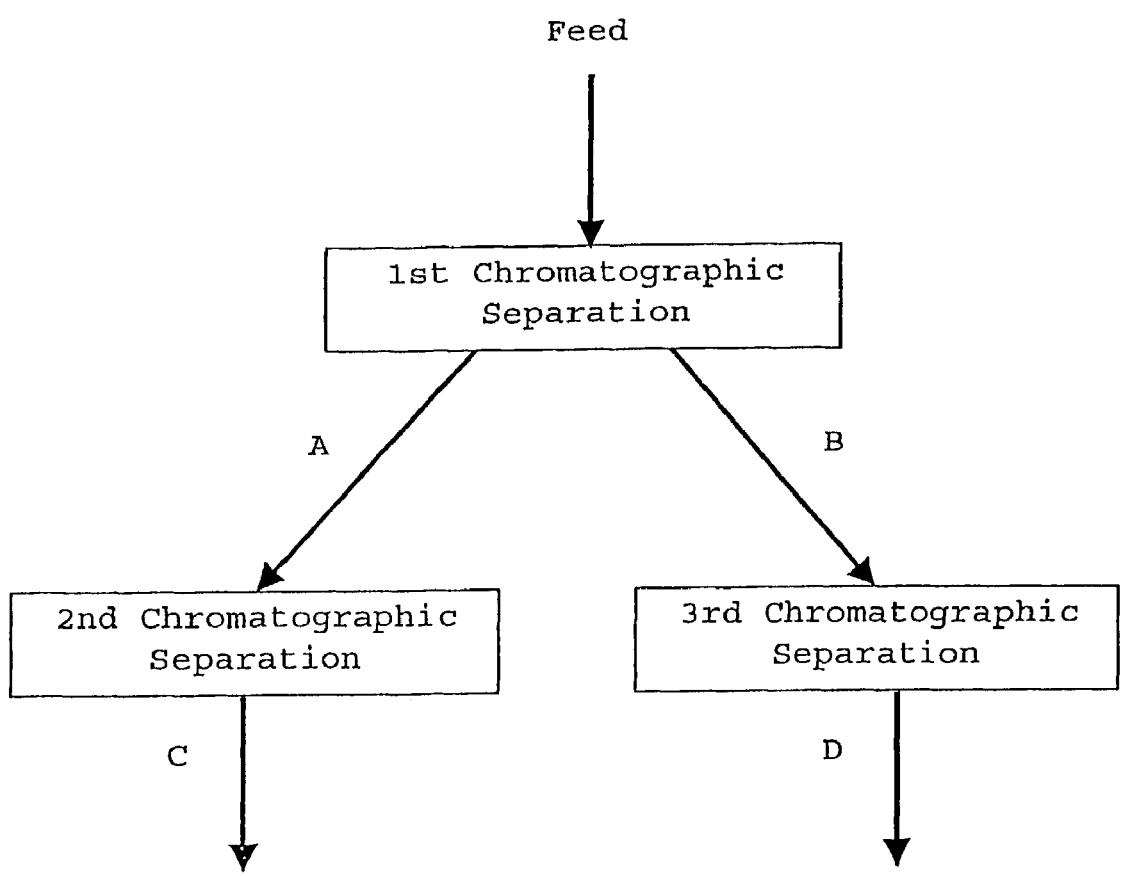
FIG. 1 schematically shows the basic layout of the process according to the present invention.

In the following the invention will be described by way of reference to a two step process. However, it should be noted that the method according to the present invention may also include additional steps.

In the first step of the method according to the present invention a liquid feed mixture or solution is subjected to a first chromatographic separation.

The composition of the feed mixture or solution is not particularly limited. However, the feed mixture or solution must be generally suited for chromatographic separation, i.e. it should be substantially free from solid insoluble impurities and of a suitable viscosity. The method is particularly suitable for the processing, upgrading or treatment of sugar beet molasses, sugar cane molasses, stillage, wheat molasses, vinasse, glucose-fructose syrup, maltose syrup, maltitol syrup, starch hydrolyzate syrups, lactose-lactulose syrup, sulphite cooking liquor and prehydrolysates as well as solutions or mixtures derived therefrom.

In the first chromatographic separation according to the present invention, at least a fraction (A) and a fraction (B) are recovered. Both fraction (A) and fraction (B) contain a first component or product. Fractions (A) and (B) need not necessarily be rich in said first component or product in the sense that they contain a higher percentage of said first component or product based on their dry matter than the feed. However, it is preferred that at least one of fractions (A) and (B) is rich in said first component or product in the aforementioned sense. It is even more preferred that both fractions are rich in said first component or product.

As far as a minimum amount of said first component or product in fraction (A) and fraction (B) is concerned, it should be noted that this minimum amount should in any case be higher than a mere incidental impurity. While concrete figures in this respect depend on the type of feed mixture used in an individual case, it can generally be noted that the amount of said first component or product in both fraction (A) and fraction (B) should be sufficiently high so as to allow for the recovery of a fraction rich in said first component or product in the second and third chromatographic separations to be discussed below. As a rough guideline, however, fractions (A) and (B) should contain at least 1% by weight based on the dry matter thereof of said first component or product. For a higher value product concentrations even less than 1% might be commercially feasible to recovery with the present invention.

In the second step of the method according to the present invention, fraction (A) and fraction (B) are separately subjected to further chromatographic separation in a second and third chromatographic separation. Fractions (A) and (B) may be introduced into said second and third chromatographic separations in the form in which they are recovered from said first chromatographic separation. However, in special cases fractions (A) and (B) can be subjected to an intermediate treatment so as to render them more suitable for further chromatographic separation. Such intermediate treatment preferably results in an increase in the dry matter content by evaporation, pH adjustment and/or alteration of ion form before said second and third chromatographic separation.

In said second chromatographic separation at least a fraction (C) is recovered and in said third chromatographic separation at least a fraction (D) is recovered. Both fractions (C) and (D) are rich in said first component or product. The term "rich" means that the weight percentage of said first component or product in the dry matter of said fraction (C) and said fraction (D) is higher than the weight percentage of said first component or product in the dry matter of the feed.

The method according to the present invention can also be used for generating further product fractions. One conceivable way of doing so is to generate one or more further fractions containing further components or even fractions rich in further components in said first chromatographic separation. If need be, such additional fractions can then be fractionated in one or more further chromatographic separations parallel to said second and said third chromatographic separations. Alternatively or additionally, it is also possible to separate further fractions in said second and/or said third chromatographic separations. Yet a further conceivable modification for the generation of additional product fractions resides in a further separation of fractions taken from said second or said third chromatographic separation or chromatographic separations parallel thereto. Such subsequent chromatographic separations will then constitute a third step of the process according to the present invention.

In a first preferred embodiment of the method according to the present invention, a fraction (E) rich in said first component or product is recovered from said first chromatographic separation. Fraction (E), if required, can be separated in a further chromatographic separation.

In a further preferred embodiment of the method according to the present invention, a fraction (F) rich in a second component or product is recovered from said first chromatographic separation. According to this embodiment of the method of the present invention it is possible to obtain two products at high yield and in high purity from a given feed mixture.

In a further embodiment of the method according to the present invention, a fraction (G) rich in a third component or product is recovered from said first chromatographic separation. Accordingly, in this embodiment of the present invention three components or products can be recovered simultaneously with high yield and high purity.

In yet a further preferred embodiment of the method according to the present invention, a fraction (H) rich in said second component or product is recovered from said second and/or said third chromatographic separation.

From said second and/or said third chromatographic separations one may also recover a fraction (I) rich in said third component, a fraction (J) rich in a fourth component or product and/or a fraction (K) rich in a fifth component or product.

In view of the above-mentioned fractions (E), (F), (G), (H), (I), (J) and (K) it should be noted that each individual fraction can be recovered independently from the other fractions. That is to say, there is no need that e.g. fraction (G) is always recovered in connection with the recovery of fractions (E) and (F). Likewise, fraction (F) can be recovered independently from fractions (E) and (G). The same is true for fractions (H), (I), (J) and (K). Of course, it is possible to recover two or more of fractions selected from (E), (F), (G), (H), (I), (J) and (K) at the same time.

It is moreover preferred according to the present invention to recover a fraction (L) in said second and/or third chromatographic separation and to reintroduce this fraction (L) into one or more of said first, second and third chromatographic separation. The recovery of a fraction (L), which usually is a mixed fraction, can be advantageous in order to improve the overall yield of the method according to the present invention. Before being reintroduced into one or more of the aforementioned chromatographic separations, fraction (L) can, of course, also be subjected to a treatment in order to render it more suitable for chromatographic separation. Such treatment could, for example, result in an increase of the dry matter content of fraction (L). In such a case the treatment of fraction (L) might involve a temporary storage in the tank or not.

Fraction (L) can be reintroduced into said first, second and/or third chromatographic separation in admixture with the feed and/or fraction (A) and/or fraction (B). However, fraction (L) can also be introduced in sequence with the feed, fraction (A) or fraction (B) respectively. In the case of simulated moving bed chromatography, it is also possible to reintroduce fraction (L) at a different point in the dry solids profile than the feed, fraction (A) and/or fraction (B) respectively.

Similarly to the recovery of fraction (L), one may also recover a fraction (M) in said first chromatographic separation and reintroduce it into said first chromatographic separation in admixture with the feed or separately therefrom. In a special embodiment fraction (M) is rich in the first component and even richer than fraction (A) or (B). In another special embodiment fraction (A) has become poorer in relation to the third component or product and fraction (B) has become poorer in relation to said second component or product.

With respect to fractions (L) and (M), it should also be noted that these fractions can be recovered independently from the recovery of one or more of the remaining fractions (E), (F), (G), (H), (I), (J) and (K). Moreover, there is no need to recover both of fractions (L) and (M) at the same time. Depending on the feed and further circumstances of the overall process it is rather possible to combine the recovery of fractions (L) and (M) with the recovery of one or more of the remaining fractions.

The first, second and third chromatographic separation may be effected by way of batch chromatographic separation or simulated moving bed chromatographic separation. The simulated moving bed chromatographic separations used according to the present invention may be continuous or sequential.

In a continuous simulated bed process all fluid streams typically flow continuously. The streams are: the supply of feed solution and eluent, the circulating or recycling of the liquid mixture and the withdrawal of products. The flow rate for these flows may be adjusted in accordance with the separation goals (yield, purity, capacity). Normally, a plurality of partial packed beds are combined into a loop. The eluent and feed supply and the product withdrawal points are shifted cyclically in the downstream direction in the packing material bed.

On account of the supply of eluent and feed solution the withdrawal of products and the flow through the packing material bed circulation, a dry solids profile is formed in the packing material bed. Constituents having a low migration rate in the packed bed are concentrated in the back slope of the separation profile, i.e. dry solids profile, while constituents having a higher migration rate are concentrated in the front slope.

The points of introduction of the feed solution and eluent and the withdrawal points of the product or products are shifted cyclically at substantially the same rate at which the dry solids profile moves in the packing material bed. The eluent and feed supply and product withdrawal points are shifted cyclically, e.g. by using feed and product valves located along the packing material bed, typically at the upstream and downstream end of each partial packed bed. If product fractions of very high purity are desired, narrow fractions and multiple partial packed beds should be employed.

In the sequential simulated moving bed process, some of the fluid streams do not flow continuously. These streams are: the supply of feed solution and eluent, the circulating or recycling of the liquid mixture and the withdrawal of products. Recycle fractions can be collected and re-fed to the system in a manner known to the skilled person.

The flow rate and the volumes of the different feeds and product fractions may be adjusted in accordance with the separation goals (yield, purity, capacity). The process commonly comprises three basic phases: feeding, elution and circulation. During the feeding phase the feed solution may be introduced into one or more predetermined partial packed beds and simultaneously a product fraction or fractions are withdrawn. During the eluting phase, eluent is introduced into a predetermined partial packed bed or predetermined partial packed beds and during these phases two or three or even four product fractions are withdrawn. During the circulating phase the dry solids profile is circulated or recycled within the partial packed beds. All three phases or a combination of two phases may occur simultaneously or partially simultaneously, but in a preferred mode no feeding phase or eluent are applied during circulation. However, the, the circulation and eluting or circulation and feeding phases can be simultaneous.

The method for effecting the chromatographic separation in said first, second, third or in further chromatographic separations of the present invention can be chosen freely. That is to say, depending on the circumstances, each chromatographic separation can independently be operated as a batch chromatographic separation, a sequential simulated moving bed chromatographic separation or a continuous simulated moving bed chromatographic separation.

Each chromatographic separation, be it a batch chromatographic method or a simulated moving bed method, may be effected in one or more chromatographic columns. The total number of columns is not particularly limited. However, for practical reasons, 1 to 20 and preferably 1 to 8 columns are used. Each column may comprise one or several separate partial packed beds.

In the case where a chromatographic separation uses a simulated moving bed method, the columns or partially packed beds form a loop. Each loop consists of at least one column, bed or part thereof, which is separate and apart from one or more of the other loops. Each loop can be open or closed.

The columns or beds are packed with suitable materials known in the art of chromatography. Particularly suited materials are, for example, gel-type strong acid cation exchange resins, such as Finex VO9C, Finex B13C, Finex CS136C (all manufactured by Finex Oy, Finland), or Purolite PCR651 (manufactured by Purolite Ltd., USA).

A preferred application of the method according to the present invention in all its embodiments is the fractionation of sucrose containing solutions, particularly sucrose containing solutions such as molasses. If such a liquid mixture is used as the feed according to the present invention, said first component or product may be raffinose, said second component or product may be sucrose, and said third component or product may be salt and said fourth component or product may be betaine. Alternatively or additionally, one of the components or products may be an amino acid fraction, a fraction containing amino acid derivatives, sugars, sugar alcohols and the like. Typical examples for such compounds include serine, inositol, γ-aminobutyric acid, glucose, fructose, PCA, galactinol, mannitol and erythritol. They are preferably recovered as said second component or product.

A further preferred starting material to be fractionated, according to the method of the present invention, are cooking liquors and here in particular sulphite cooking liquors. If such sulphite cooking liquors are used as the liquid feed mixture, the first component or product may be xylose, the second component or product may be xylonic acid or an acetic acid fraction and a suitable third component or product may be lignosulphonates and/or salts.

In the following, the present invention will be illustrated by way of specific examples. With respect to the equipment, individual conditions, dimensions and materials mentioned in the examples below, it should be noted that while these details are referred to in the specific context of the examples, they each individually represent typical features of the method of the present invention and are thus also illustrative of the present invention when considered in isolation. Numerical values contained in the examples are also illustrative of the respective ranges according to the present invention.

EXAMPLE 1

Xylose Separation from Sulphite Cooking Liquor

The test equipment in SMB-chromatographic mode included four columns connected in series, feed pumps, recycling pumps, eluent water pumps as well as inlet and product valves for the various process streams. The height of each column was 5 m and each column had a diameter of 0.2 m. The columns were packed with a strong acid gel type cation exchange resin (Finex CS13GC) in $Mg^{2+}$-form. The mean bead size was 0.36 mm and the divinylbenzene content 6.5%.

The first two columns formed a first loop for the first chromatographic separation. The third column formed a second loop for the second chromatographic separation, and the fourth column formed a third loop for the third chromatographic separation.

As a feed, sulphite cooking liquor from an $Mg^{2+}$-based cooking process was used and the aim was to separate the xylose contained therein.

The liquor was filtered using diatomaceous earth as a filter aid and diluted to a D.S. concentration of 48 wt.-%. The pH was 3.3.

The sulphite cooking liquor was composed as set forth below, whereby the percentages are given on a dry substance weight basis.

| Composition of Feed | on % DS |
|---|---|
| Xylose | 19.1 |
| Glucose | 1.9 |
| Galactose + rhamnose | 1.8 |
| Mannose | 2.2 |
| Lignosulphonates | 42.6 |
| Xylonic acid | 6.1 |
| Others | 26.3 |

The fractionation was performed by way of a 7-step sequence as set forth below. The feed was used at a temperature of 65° C. and water was used as an eluent.

Step 1: 19 l of feed solution were pumped into the first column at a flow rate of 80 l/h, firstly 5 l of recycle and then 14 l of xylose were collected from column 3. Simultaneously 35 l of liquid were circulated in loop 3 (column 4) at a flow rate of 150 l/h.

Step 2: 32 l were circulated in loop 2 (column 3) at a flow rate of 100 l/h. Recycle was not collected.

Step 3: 19 l of feed solution were pumped to the first column at a flow rate of 100 l/h and from the same column a first residual fraction was collected. Simultaneously 19 l of water were pumped to column 2 at a flow rate of 100 l/h and 2 l of recycle fraction followed by 14 l of xylose and finally 3 l of recycle fraction were collected from column 4. Simultaneously also 20 l of water were pumped to column 3 at a flow rate of 80 l/h and a residue fraction was collected from column 3.

Step 4: 15 l of water were pumped to column 2 at a flow rate of 150 l/h and a residue fraction was collected from column 1. Simultaneously 14 l were circulated in loop 2 (column 3) at a flow rate of 80 l/h. At the same time 14 l were circulated in loop 3 (column 4) at a flow rate of 80 l/h.

Step 5: 45 l were circulated in loop 1 (columns 1 and 2) at a flow rate of 150 l/h. Simultaneously 20 l of water were pumped to column 4 at a flow rate of 80 l/h and a residual fraction was collected from column 4.

Step 6: 60 l of water were pumped to column 1 at a flow rate of 150 l/h and a residue fraction was collected from column 2.

Step 7: 30 l were circulated in loop 1 (columns 1 and 2) at a flow rate of 150 l/h.

After equilibration of the system, the following fractions were drawn from the system: residue fractions from each column, xylose containing fractions from columns 3 and 4 as well as one recycle fraction from column 3 and two recycle fractions from column 4. All residue fractions were combined, both xylose fractions were combined and all recycle fractions were combined and subjected to HPLC analysis. The results are set forth in the Table below. The overall xylose yield calculated from these fractions was 86.4%.

| Fraction (combined) | Xylose | Residual | Recycle |
|---|---|---|---|
| Volume, l | 28.0 | 134 | 10.0 |
| Dry solids, g/100 ml | 19.0 | 11.6 | 16.4 |
| Xylose, % DS | 54.0 | 2.9 | 47.7 |
| Glucose, % DS | 3.3 | 1.1 | 4.4 |
| Galactose + rhamnose, % DS | 5.1 | 0.3 | 4.5 |
| Mannose, % DS | 6.0 | 0.6 | 5.7 |
| Others, % DS | 31.6 | 95.2 | 37.8 |

EXAMPLE 2

Xylose Separation from Sulphite Cooking Liquor

The test equipment in SMB-chromatographic mode included four columns connected in series, feed pumps, recycling pumps, eluent water pumps and inlet and product valves for the different process streams. The height of each column was 5 m and each column had a diameter of 0.2 m. The columns were packed with Finex CS13GC strong acid cation exchange resin in the $Mg^{2+}$-form. The mean bead size of the resin was 0.36 mm and the divinylbenzene content was 6.5%.

The first two columns formed the first loop for the first chromatographic separation. The third column functioned as a second loop for the second chromatographic separation and the fourth column functioned as a third loop for the third chromatographic separation. The columns were operated at 65° C. at a flow rate of 80, 100 and 150 l/h, respectively.

The feed was a sulphite cooking liquor with the following composition. The liquor was subjected to the same workup procedure as set forth in example 1.

| Composition of Feed | % DS |
|---|---|
| Xylose | 19.6 |
| Glucose | 2.0 |
| Galactose + rhamnose | 1.1 |
| Mannose | 2.1 |
| Others | 75.2 |
| pH | 3.8 |

The fractionation was performed in 7 steps. The duration of the sequence was 87 minutes. The individual steps were as follows:

Step 1: 16 l of feed solution were pumped into the first column at a flow rate of 80 l/h, firstly 2 l of recycle and then 12 l of xylose and finally 2 l of recycle were collected from column 3. Simultaneously 39 l of liquid were circulated in loop 3 at a flow rate of 150 l/h.

Step 2: 6 l of feed solution were pumped into the first column at a flow rate of 80 l/h and from column 2 recycle was collected. Simultaneously 35 l were circulated in loop 2 at a flow rate of 100 l/h.

Step 3: 16 l of feed solution were pumped into the first column at a flow rate of 100 l/h and from the same column residual 1 was collected. Simultaneously 16 l water were pumped into column 2 at a flow rate of 100 l/h, and firstly 2 l recycle and then 12 l xylose and finally 2 l recycle were collected from column 4. Simultaneously also 20 l water were pumped into column 3 at a flow rate of 80 l/h and residual 3 was collected from column 3.

Step 4: 15 l water were pumped into column 2 at a flow rate of 150 l/h and residual 1 was collected from column 1. Simultaneously 16 l were circulated in loop 2 at a flow rate of 80 l/h. Simultaneously also 17 l were circulated in loop 3 at a flow rate of 80 l/h.

Step 5: 55 l were circulated in loop 1 at a flow rate of 150 l/h. Simultaneously 16 l water were pumped to column 4 at a flow rate of 80 l/h and residual 4 was collected from column 4.

Step 6: 50 l water were pumped into column 1 at a flow rate of 150 l/h and residual 2 was collected from column 2.

Step 7: 30 l were circulated in loop 1 at a flow rate of 150 l/h.

After equilibration of the system, product fractions were collected. That is to say, 11 fractions were withdrawn. These fractions were a residual fraction recovered from each column, a xylose fraction recovered from columns 3 and 4, a recycle fraction recovered from column 2, two recycle fractions recovered from column 3 and two recycle fractions recovered from column 4. All residual fractions were combined, both xylose fractions were combined and all recycle fractions were combined and then analysed. The results of the analysis are summarized in the Table below. The xylose yield calculated from the product fractions was 81.7%. The recycle fraction from column 2 was mixed into the feed solution.

| Fraction (combined) | Xylose | Residual | Recycle |
|---|---|---|---|
| Volume, l | 24.0 | 117 | 14.0 |
| Dry solids, g/100 ml | 17.4 | 12.9 | 20.3 |
| Xylose, % DS | 55.0 | 3.4 | 47.4 |
| Glucose, % DS | 3.3 | 1.1 | 3.4 |
| Galactose + rhamnose, % DS | 6.0 | 0.0 | 5.2 |
| Mannose, % DS | 5.6 | 0.6 | 5.1 |
| Others, % DS | 30.1 | 94.9 | 39.0 |
| pH | 4.0 | 3.6 | — |

EXAMPLE 3

Raffinose Purification from Molasses Separation

The test equipment included three SMB-sets each with four columns. The columns in each set were connected in series and included feed and eluent pumps, recycling pumps and inlet and product valves for the different process streams. The sets were operated under sequential SMB conditions.

The height of each column in the first loop was 5.0 m, in the second loop 2.6 m and in the third loop 3.5 m. The diameter of each column was 0.11 m. All columns were packed with Na+ form gel type strong acid cation exchange resin (FINEX). The mean bead size of the resin was 0.36 mm and DVB content 6.5%.

The first SMB-set composed the first loop for the first chromatographic separation, the second set functioned as the second loop for the second chromatographic separation and the third set functioned as the third loop for the third chromatographic separation.

The feed material was beet molasses. The molasses was diluted to 60 Bx and carbonated with sodium carbonate (1.5% on DS basis, temperature 60° C., 3 h reaction time). The carbonated solution was filtered with a Seitz pressure filter using Kenite 300 as a filtering aid (precoat 1 kg/m², bodyfeed 0.5% on DS basis). After this, the pH was adjusted with HCl to pH 8.8 from 9.0. The feed concentration was adjusted to 68 g/100 ml (approximately 55 Bx). The composition is set forth in the Table below.

| Feed | % on D.S. |
|---|---|
| Sucrose | 60.6 |
| Raffinose | 1.7 |
| Betaine | 6.6 |
| Others | 31.1 |

In the first loop, the above feed was split into several fractions. Fraction (A) and fraction (B) were enriched with raffinose. Fraction (A) contained salts, raffinose and sucrose eluting before fraction (B). Fraction (B) was mainly salts, raffinose and sucrose eluting before the sucrose fraction. The compositions of the fractions are set forth below.

| Fraction (A) | |
|---|---|
| Concentration, g/100 ml | 6.8 |
| Sucrose, % DS | 3.0 |
| Raffinose, % DS | 4.9 |
| Betaine, % DS | 0.0 |
| Others, % DS | 92.1 |

| Fraction (B) | |
| --- | --- |
| Concentration, g/100 ml | 17.5 |
| Sucrose, % DS | 61.5 |
| Raffinose, % DS | 3.5 |
| Betaine, % DS | 0.0 |
| Others, % DS | 34.9 |

Said fractions (A) and (B) were then fed into the third and second loop respectively. In the second and third loops these fractions were then fractionated further by way of sequential SMB chromatography.

The following Table summarises the composition of the various fractions taken in the first, second or third loop as well as the composition of the combined fractions.

| Loop 1 fractions | Sucrose | Betaine | Residual | Fraction (B) Raffinose for loop 2 | Fraction (A) Raffinose for loop 3 |
| --- | --- | --- | --- | --- | --- |
| Volume, l | 13.5 | 14.0 | 35.0 | 7.5 | 10.5 |
| Dry solids, g/100 ml | 25.6 | 3.8 | 2.8 | 17.5 | 6.8 |
| Sucrose, % Ds | 94.8 | 9.5 | 9.8 | 61.5 | 3.0 |
| Raffinose, % Ds | 0.8 | 0.0 | 1.0 | 3.5 | 4.9 |
| Betaine, % Ds | 0.0 | 82.4 | 1.9 | 0.0 | 0.0 |
| Others, % Ds | 4.4 | 8.1 | 87.4 | 34.9 | 92.1 |
| Loop 2 fractions | Raffinose | Sucrose | Residual | Recycle | |
| Volume, l | 4.2 | 3.4 | 9.5 | 3.2 | |
| Dry solids, g/100 ml | 4.4 | 18.1 | 1.7 | 10.2 | |
| Sucrose, % Ds | 2.2 | 95.1 | 0.5 | 62.3 | |
| Raffinose, % Ds | 10.6 | 1.1 | 1.4 | 5.0 | |
| Betaine, % Ds | 0.0 | 0.0 | 0.0 | 0.0 | |
| Others, % Ds | 87.2 | 3.7 | 98.1 | 32.7 | |
| Loop 3 fractions | Raffinose | Residual | | | |
| Volume, l | 8.0 | 24.0 | | | |
| Dry solids, g 100/ml | 3.2 | 1.9 | | | |
| Sucrose, % Ds | 0.8 | 4.2 | | | |
| Raffinose, % Ds | 9.5 | 2.3 | | | |
| Betaine, % Ds | 0.0 | 0.0 | | | |
| Others, % Ds | 89.7 | 93.5 | | | |
| Combined fractions | Raffinose | Sucrose | Residual | Recycle | Betaine |
| Volume, l | 12.2 | 16.9 | 68.5 | 3.2 | 14.0 |
| Dry solids, g/100 ml | 3.6 | 24.0 | 2.4 | 10.9 | 3.8 |
| Sucrose, % Ds | 1.4 | 94.8 | 7.3 | 62.3 | 9.5 |
| Raffinose, % Ds | 10.0 | 0.9 | 1.4 | 5.0 | 0.0 |
| Betaine, % Ds | 0.0 | 0.0 | 1.1 | 0.0 | 82.4 |
| Others, % Ds | 88.6 | 4.3 | 90.5 | 32.7 | 8.1 |

The overall yield calculated from the product fractions was 95.2% for sucrose, 96.0% for betaine and 32.2% for raffinose.

The invention claimed is:

1. Method of fractionating liquid mixtures or solutions, comprising the steps of
subjecting a feed in the form of a liquid mixture or solution comprising three or more components to a first chromatographic separation, thereby recovering at least a fraction (A) and a fraction (B) both containing a first component or product, which is in the middle of eluting components in a dry solids profile of said eluting components,
subjecting a mixture or solution derived from or comprising said fraction (A) to a second chromatographic separation, thereby recovering at least a fraction (C) which has a higher weight percentage of said first component or product than the feed, and
subjecting a mixture or solution derived from or comprising said fraction (B) to a third chromatographic separation, thereby recovering at least a fraction (D) which also has a higher weight percentage of said first component or product than the feed, and whereby at least two fractions are recovered from the second and third chromatographic separations.

2. Method according to claim 1, wherein said first and/or said second and/or said third chromatographic separations are effected by way of a simulated moving bed method.

3. Method according to claim 1, wherein said first chromatographic separation is effected by way of a simulated moving bed method and said second and third chromatographic separations are effected by way of batch chromatographic methods.

4. Method according to claim 1, wherein in said first chromatographic separation a fraction (E) rich in said first component or product is recovered.

5. Method according to claim 1, wherein in said first chromatographic separation a fraction (F) rich in a second component or product is recovered.

6. Method according to claim 5, wherein said second component or product is sucrose.

7. Method according to claim 5, wherein said second component or product is an acetic acid or an acetic acid containing fraction.

8. Method according to claim 1, wherein in said first chromatographic separation a fraction (G) rich in a third component or product is recovered.

9. Method according to claim 8, wherein said third component or product is salt.

10. Method according to claim 1, wherein in said second and/or said third chromatographic separation a fraction (H) rich in said second component or product is recovered.

11. Method according to claim 1, wherein in said second and/or third chromatographic separation a fraction (I) rich in said third component or product is recovered.

12. Method according to claim 1, wherein in said first, second and/or third chromatographic separation a fraction (J) rich in a fourth component or product is recovered.

13. Method according to claim 12, wherein said fourth product is betaine.

14. Method according to claim 5 or claim 12, wherein said second and/or fourth component or product is xylonic acid.

15. Method according to claim 6 or claim 12, wherein said third and/or fourth component or product is lignosulphonate.

16. Method according to claim 1, wherein in said first, second and/or third chromatographic separation a fraction (K) rich in a fifth component or product is recovered.

17. Method according to claim 1, wherein a fraction (L) is recovered in said second and/or third chromatographic separation and returned into said first, second and/or third chromatographic separation.

18. Method according to claim 17, wherein fraction (L) is admixed with said feed and/or said mixture or solution derived from or comprising fraction (A) and/or said mixture or solution derived from or comprising fraction (B).

19. Method according to claim 1, wherein a fraction (M) is recovered in said first chromatographic separation and returned into said first chromatographic separation.

20. Method according to claim 19, wherein fraction (M) is admixed with said feed.

21. Method according to claim 1, wherein said fraction (M) is rich in the first component.

22. Method according to claim 1, wherein said fraction (A) and fraction (B) have become poorer in relation to the second or third component or product respectively.

23. Method according to claim 1, wherein said feed is sugar beet molasses, sugar cane molasses, wood molasses or wheat molasses.

24. Method according to claim 23, wherein said first component or product is raffinose.

25. Method according to claim 1, wherein said feed is sulphite cooking liquor.

26. Method according to claim 25, wherein said first component or product is xylose.

27. Method according to claim 1 wherein the feed is selected from stillage, vinasse, glucose-fructose syrup, maltose syrup, maltitol syrup, starch hydrolyzate syrups, lactose-lactulose syrup and prehydrolysates as well as solutions or mixtures derived therefrom.

28. Method according to claim 1, wherein the simulated moving bed chromatographic separation is sequential or continuous.

29. Method according to claim 28, wherein the loops are open and/or closed.

30. Method according to claim 29, wherein a solution derived from a fraction in one of the loops is transferred or passed to another loop when the loops are open.

31. Method according to claim 28, wherein each loop comprises a series of columns, beds or parts thereof and each loop has at least one column, bed or part thereof which is separate and apart from one or more of the other loops.

32. Method according to claim 28, wherein each loop is separate and distinct from the other.

33. Method according to claim 1, wherein one or more of the chromatographic separations is effected with the aid of a strong acid cation exchange resin.

34. Method according to claim 1, wherein water is used as an eluent.

35. Method according to claim 1, wherein at least said second and third chromatographic separations are effected in parallel loops.

36. Method according to claim 1, wherein fractions taken from said second and/or third chromatographic separation are subjected to further chromatographic separation in one or more further loops which may be parallel.

* * * * *